United States Patent [19]
Carr

[11] Patent Number: 5,616,268
[45] Date of Patent: Apr. 1, 1997

[54] MICROWAVE BLOOD THAWING WITH FEEDBACK CONTROL

[75] Inventor: Kenneth L. Carr, Harvard, Mass.

[73] Assignee: Microwave Medical Systems, Littleton, Mass.

[21] Appl. No.: 271,852

[22] Filed: Jul. 7, 1994

[51] Int. Cl.$^6$ .............................. H05B 6/80; H05B 6/68
[52] U.S. Cl. .................... 219/687; 219/710; 219/709; 219/703; 219/748; 604/114
[58] Field of Search .................... 219/687, 703, 219/709, 710, 712, 711, 717, 718; 604/748, 113, 114

[56] References Cited

U.S. PATENT DOCUMENTS

| | | | |
|---|---|---|---|
| 4,251,437 | 2/1981 | Rasmussen et al. | 260/112 B |
| 4,314,143 | 2/1982 | Bilstad et al. | 219/497 |
| 4,336,435 | 6/1982 | Kashyap et al. | 219/10.55 F |
| 4,346,716 | 8/1982 | Carr | 128/653 |
| 4,471,193 | 9/1984 | Walter | 219/710 |
| 4,503,307 | 3/1985 | Campbell et al. | 219/10.55 E |
| 4,531,941 | 7/1985 | Zasuwa | 604/113 |
| 4,614,514 | 9/1986 | Carr et al. | 604/113 |
| 4,652,712 | 3/1987 | Zeipel | 219/10.55 F |
| 4,714,812 | 12/1987 | Haagensen et al. | 219/748 |
| 4,715,727 | 12/1987 | Carr | 374/122 |
| 4,801,777 | 1/1989 | Auerbach | 219/10.55 M |
| 4,871,891 | 10/1989 | Steers et al. | 219/10.55 B |
| 4,874,915 | 10/1989 | Harms et al. | 219/687 |
| 5,036,172 | 7/1991 | Kokkeler et al. | 219/10.55 M |
| 5,073,167 | 12/1991 | Carr et al. | 604/114 |
| 5,134,263 | 7/1992 | Smith et al. | 219/10.55 M |
| 5,170,024 | 12/1992 | Hanatani et al. | 219/10.55 B |
| 5,180,896 | 1/1993 | Gibby | 219/687 |
| 5,254,819 | 10/1993 | Yoshino et al. | 219/709 |

OTHER PUBLICATIONS

Webster et al., "Encyclopedia of Medical Devices and Instrumentation", vol. 4, Jun., 1988, pp. 2746–2759.

*Primary Examiner*—Philip H. Leung
*Attorney, Agent, or Firm*—Fish & Richardson P.C.

[57] ABSTRACT

A microwave thawing system for thawing bags of frozen blood products features non-invasively monitoring the internal temperature of the blood product during thawing, and controlling the level of warming energy applied to the blood product based on the monitored temperature. The non-invasive monitoring is performed with one or more antennas which receive electromagnetic energy from the frozen blood product during thawing. Because the applied energy level is controlled based on the temperature of the blood, the blood can be thawed rapidly with little risk of damage from overheating. Pressure is applied to the bag to maintain a uniform distribution of blood within the bag and to separate the thawed blood from the still-frozen blood during thawing; for example, the pressure moves the liquid blood to the periphery of the bag and retains the frozen blood in the center of the bag. As a result, the continued application of thawing energy to the frozen blood poses little risk of overheating (and contaminating) the liquid blood. The warming energy and the electromagnetic energy are transmitted and received, respectively, through transmit/receive waveguides configured to provide high isolation between its transmit and receive ports.

14 Claims, 8 Drawing Sheets

MICROWAVE BLOOD THAWING WITH FEEDBACK CONTROL

BACKGROUND OF THE INVENTION

The invention relates to thawing frozen blood products.

In hospitals, for example, blood products (e.g., red blood cells, platelets, and plasma) are stored and frozen in sealed bags for later use. These frozen blood components are generally stored at temperatures below −18° C. Red blood cells, however, are stored at temperatures below −65° C. due to the addition of glycerol, which prevents cell damage during the quick-freeze process. When the blood product is needed (e.g., for a surgical procedure), the frozen blood product is typically thawed by immersing the bag in a warm water bath for a period (e.g., 20 minutes) sufficient to thaw the blood. Alternatively, the bag of frozen blood product may be thawed by heating it within a conventional microwave oven.

SUMMARY OF THE INVENTION

This invention features non-invasively monitoring the internal temperature of a frozen blood product during thawing, and controlling the level of warming energy applied to the blood product based on the monitored temperature. In one general aspect of the invention, the non-invasive monitoring is performed with an antenna which receives electromagnetic energy from the frozen blood product during thawing.

The invention permits the frozen blood product to be rapidly and safely thawed at temperatures sufficiently low (e.g., less than 20° C.) to avoid damaging the blood product without risk of bacterial contamination (which is a concern with warm water baths). Moreover, when applied to a bag of frozen glycerolized red blood cells, the invention allows the blood product (normally stored below −65° C.) to be safely thawed in generally less than five minutes, so that the amount of pre-thawed blood required to be kept on hand can be drastically reduced. This is particularly advantageous in view of current Food and Drug Administration (FDA) regulations requiring that pre-thawed blood be disposed of if not used within 24 hours.

Preferred embodiments include the following features.

The level of the warming energy applied (e.g., transmitted by an energy source) to the blood is decreased in response to detected increases in the temperature of the blood product, as indicated by the level of electromagnetic energy from the blood product. In one monitoring approach, the detected electromagnetic energy is the blood product's emissivity (i.e., so-called "black body" thermal noise), which increases as the temperature of the blood product rises. In this case, a radiometer measures the emissivity and in response generates a control signal to adjust the output level of the energy source. Preferably, the radiometer detects the emissivity of the blood product at a frequency (e.g., 4.0 GHz) greater than the frequency of the transmitted warming energy, which is generally between 300 MHz and 3.0 GHz.

In another monitoring approach, the electromagnetic energy includes reflections of the transmitted warming energy from the blood product caused by the impedance mismatch between the blood product and the antenna. The reflections increase, as does the mismatch, when the blood product thaws, and the control signal is generated based on the amplitude of the reflected energy. In one embodiment, the warming energy transmitted to the blood product is provided by individual amplifiers, the gain of which is varied on the basis of the control signal. Alternatively, the warming energy is transmitted through a diode switching modulator, the duty cycle of which is varied by the control signal to adjust the transmitted energy level.

A plurality of antennas are used to transmit the warming energy to the blood product, so that the blood product is heated uniformly for rapid and even thawing. At least one of the antennas is positioned to receive the electromagnetic energy from the blood product. In one embodiment, each antenna receives the electromagnetic energy, and a separate control signal is generated for each antenna so that the transmitted energy level can be controlled individually for each antenna. The antennas are proximately positioned and spaced from each other along outer surfaces of the blood product to provide uniform distribution of the warming energy and to reduce the risk of "hot-spots" (i.e., areas of intense heat caused by poorly defined heating patterns) that are common with conventional microwave ovens.

Another aspect of the invention features applying pressure to a bag containing blood product, at least a portion which is partially frozen, to separate thawed portions of the blood product from frozen portions of the blood product during thawing. As a result, the applied energy can be concentrated where it is needed—on the portions of the blood product that remain frozen—without subjecting the thawed blood to additional, possibly damaging heating.

Preferred embodiments may include one or more of the following features.

The bag is supported within a cavity of a housing, and the energy is applied to the cavity from a transmitter. The applied pressure moves the thawed liquid portions from the central region of the bag toward the periphery of the bag. Thus, the blood (both liquid and frozen portions) does not settle in the bottom of the bag (where it would be more difficult to thaw efficiently). The frozen portions are retained within central regions of the bag located in the area of the cavity that receives the greatest amount of the energy from the transmitter. The bag is vertically positioned within the housing to allow air within the bag to rise to an upper end of the bag in response to the applied pressure. The bag is vibrated during thawing to encourage mixing of the thawed blood with the frozen blood.

The pressure is applied by one or more expansion bladders positioned within and along an inner surface of a cavity wall. The expansion bladder is inflated by an inflation source to a preselected pressure level, whereupon energy from the transmitter is applied to the cavity. The expansion bladder includes a number of rounded inflatable cushions formed on a surface that contacts the bag. The expansion bladder includes a thermally conductive surface that contacts the bag. The bladder is inflated with a medium which provides cooling to the surface of the bag so that heat generated in the blood near the surface of the bag, where the level of transmitted energy is highest, is drawn out of the blood. Thus, the risk of overheating is reduced and a uniform distribution of the temperature of the thawing blood from one side of the bag to the other side of the bag is maintained.

The cavity is defined by a pair of opposing walls, which are hinged at a first end of the housing so that one of the walls pivots outwardly with respect to the other wall to provide access to the cavity. A plurality of antennas, disposed within the walls, transmit the energy into the cavity. A rotary coaxial joint positioned at the first end of the housing allows the transmission of energy to antennas in one of the opposing walls while allowing the walls to pivot outward with respect to each other. The housing includes an electromagnetically shielded surface to avoid microwave energy radiating externally to the housing.

Another aspect of the invention features a dual mode (transmit/receive) transducer for use in thawing blood as discussed above. Simply put, the transducer includes a pair of waveguides—one for transmission, the other for reception—which share an aperture through which energy is transmitted to and received from a target (e.g., the frozen blood product). The transmit waveguide has a dimension selected to propagate energy injected from a transmit port in a first frequency range within the transmit waveguide and for to the target via the aperture, and to receive signals in a second, different frequency range from the target and pass them to the receive waveguide. The receive waveguide has a dimension selected to propagate the signals in the second frequency range within the receive waveguide to a receive port while substantially attenuating signals in the first frequency range. The selected dimension of the transmit waveguide and the selected dimension of the receive waveguide are positioned orthogonally to each other.

The orthogonal positioning of the waveguides and the orientation of the transmit and receive ports in their respective waveguides provides a high degree of isolation between the ports. As a result, a single, compact transducer can be used to both transmit the thawing energy to, and receive the electromagnetic energy from, the frozen blood product.

In preferred embodiments, the dimension of the receive waveguide is selected so that the signals propagating in the second frequency range within the receive waveguide have an electric field orientation transverse to the electric field orientation of the signals in the first frequency range. As a result, the received energy signals propagating within the receive waveguide have an orientation transverse to the transmitted microwave energy signals propagating in the transmit waveguide. The difference in orientation of the signals being transmitted and received provides additional isolation between the transmit and receive ports.

The receive waveguide has a second dimension orthogonal to its selected dimension for substantially attenuating second harmonics of the signals in the first frequency range, resulting in a further increase in isolation between the signals received at the transmit and receive ports. The transmit waveguide has a second dimension, orthogonal with respect to its selected dimension, selected to limit propagation of the signals in the first frequency range received at the transmit port to the $TE_{10}$ mode (the dominant mode of propagation in a rectangular waveguide). Similarly, the receive waveguide has a second dimension, orthogonal with respect to its selected dimension, selected to limit propagation of the signals in the second frequency range received at the receive port to the $TE_{10}$ mode. The selected second dimensions of the transmit and receive waveguides ensure that the signals of interest received at the transmit and receive ports are limited to electric field orientations transverse to each other.

The transmit and receive ports each include a probe which extends into their respective waveguides. The probes are mutually orthogonal to the longitudinal axis of the transmit waveguide. The receive probe is connected to circuitry for controlling the level of the transmit signals applied to the transmit port in response to signals received at the receive port.

Other features and advantages of the invention will become apparent from the following detailed description, and from the claims.

DESCRIPTION OF THE PREFERRED EMBODIMENTS

Figure 1:
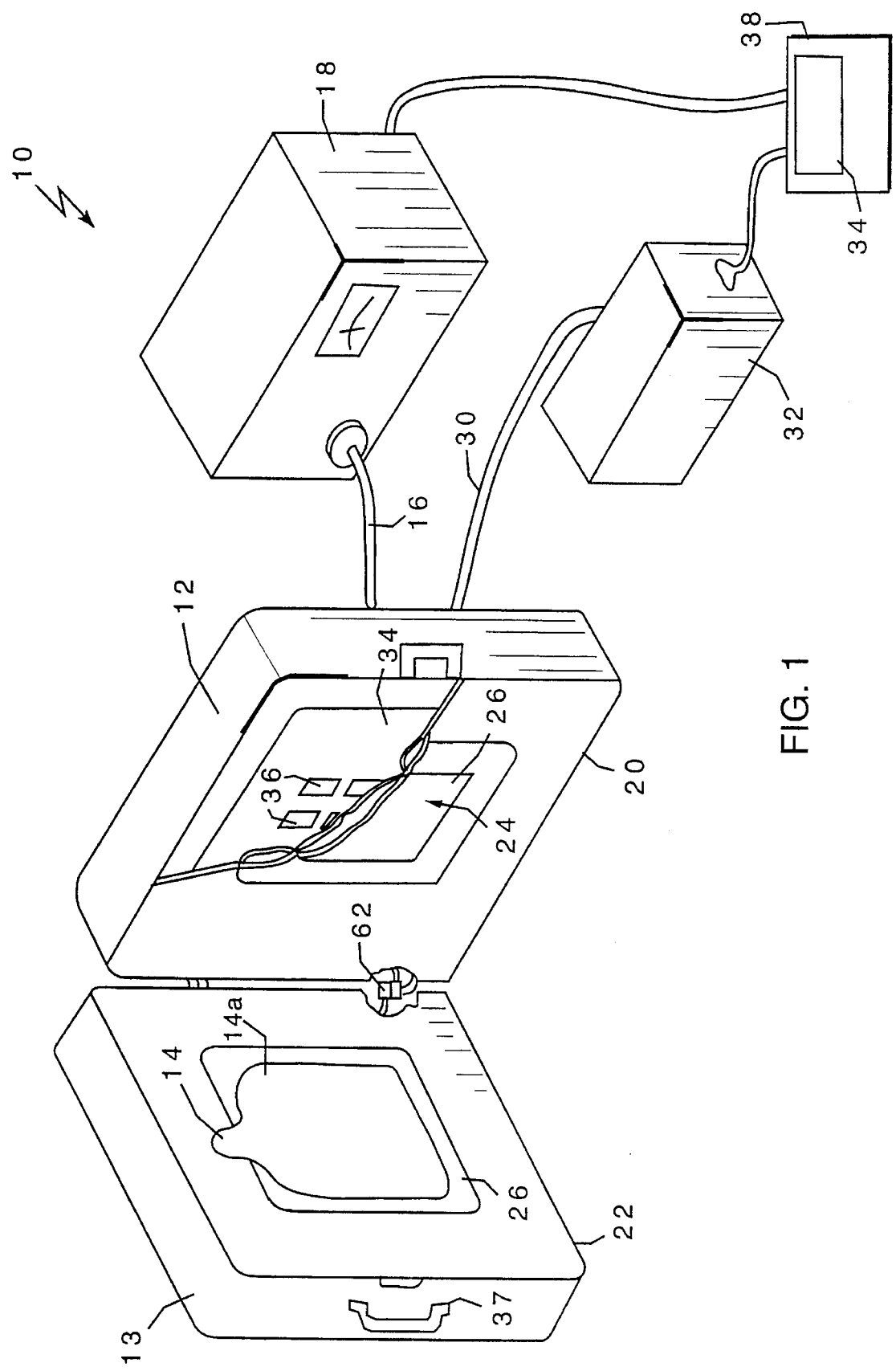
FIG. 1 shows a microwave system for thawing a blood product.

Referring to FIG. 1, system 10 for thawing a bag 14 of frozen blood (e.g., glycerolized red blood cells) 15 includes a portable thawing unit 12 within which bag 14 is supported. Bag 14 is made of a microwave transmissive material, such as plastic, and holds approximately 680 ml of blood (i.e., one unit). Thawing unit 12 includes a housing 13 having a pair of hinged door panels 20, 22 which together define an internal pressure infusion chamber 24 for receiving bag 14. Pressure infusion chamber 24 is formed within the interior and central portions of door panels 20, 22 by a pair of inflatable bladders 26, one in each door panel, that are connected by a hose 30 to a compressor 32.

Positioned behind bladders 26 are antenna arrays 34, 35 (only array 34 is shown), comprising waveguide heating elements 36 directed toward broad surfaces 14a, 14b of bag 14. Antenna arrays 34, 35 receive microwave energy at a frequency of 2.45 GHz from an external microwave power source 18 (available from Microwave Medical Systems, Littleton, Mass.) connected to thawing unit 12 through a power cable 16. Housing 13 includes metal shielding for preventing microwave energy from escaping from the enclosure during operation of thawing unit 12. Thawing unit 12 is portable, and includes a handle 37 for easy transport.

A computer 38, operating in response to a stored program, controls the activation of power source 18 and compressor 32 and synchronizes their operation. As described in detail below, computer 38 activates compressor 32 to inflate bladders 26 to a selected pressure against bag 14, and then triggers power source 18 to apply microwave thawing energy to arrays 34, 35. Computer 38 also records and stores operational and statistical data, and includes a display screen 39 for displaying the monitored blood temperature and the time remaining in the thaw cycle.

Figure 2:
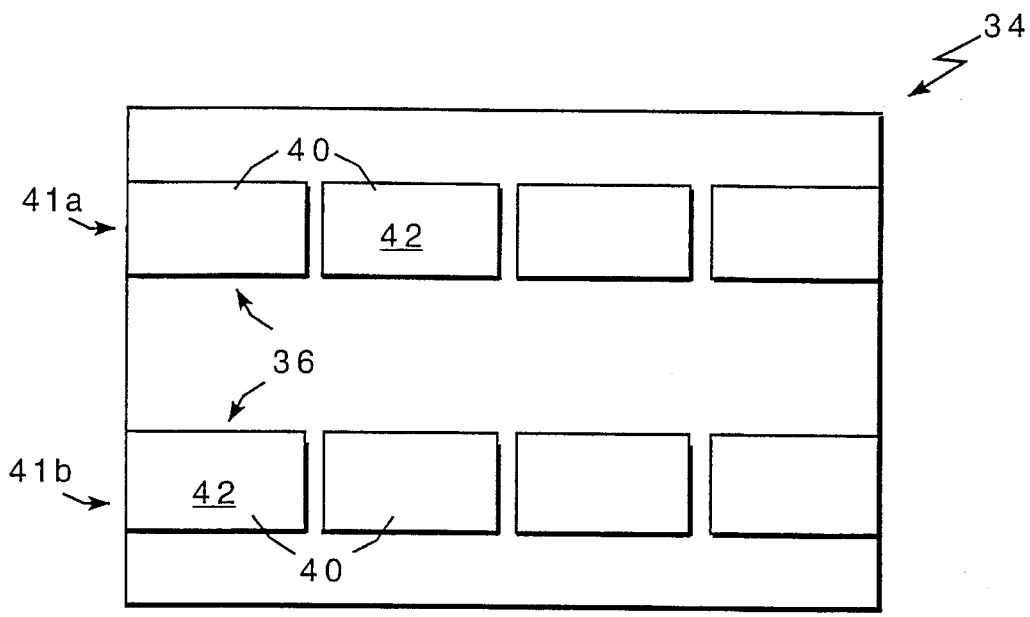
FIG. 2 is a front view of one of the antenna arrays of the system of FIG. 1.

Referring to FIG. 2, a front view of antenna array 34 is shown. Array 34 includes waveguide heating elements 36 arranged in two rows 41a, 41b of four elements each. (Antenna array 35, supported within door panel 22, has an identical arrangement.) Each waveguide heating element 36 includes a transmit/receive antenna 40 having a rectangularly shaped aperture 42 facing broad surface 14a of bag 14. Heating elements 36 are spaced closely (about 0.35 inches apart) so that array 34 is relatively compact in size (8.6"× 5.0"). Arrays 34, 35 are positioned adjacent to only the central region of bag 14 so that the periphery of bag 14 is subjected to substantially less microwave energy than the central region of bag 14. Transmit/receive antennas 40 simultaneously transmit microwave warming energy to bag 14 for heating blood 15 and receive electromagnetic radiant energy from blood 15, such as the emissivity (i.e., passive electromagnetic noise energy) radiated by blood 15.

Figure 3:
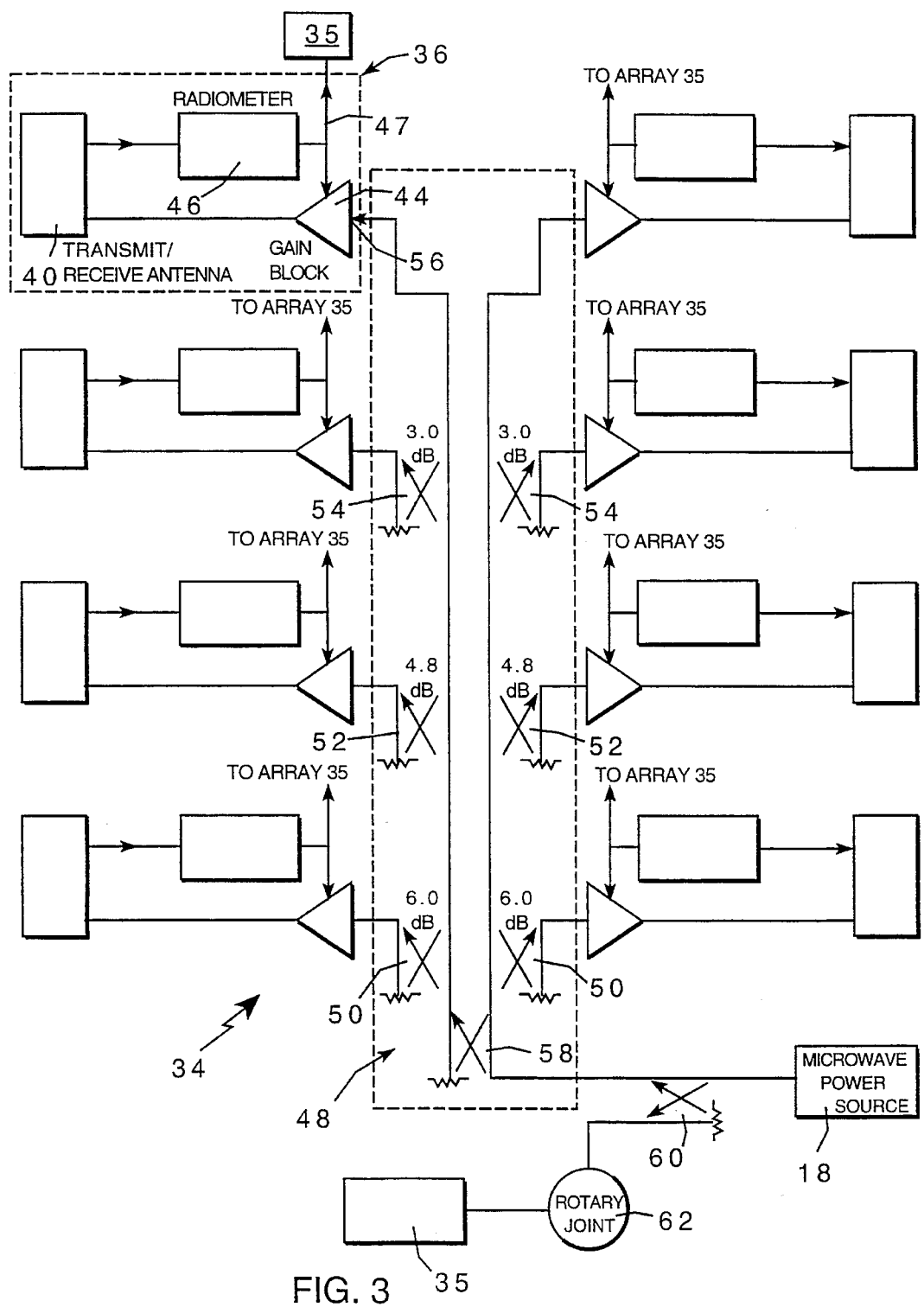
FIG. 3 is a schematic diagram of one of the microwave power distribution networks of the system of FIG. 1.

Referring also to FIG. 3, each heating element 36 of array 34 includes a variable gain amplifier 44 for applying microwave energy to transmit/receive antenna 40, and a radiometer 46 for controlling the gain of amplifier 44 in response to the electromagnetic radiant energy received by transmit/receive antenna 44. The emissivity of blood 15 increases as its temperature increases, and thus radiometers 46 generate gain control signals which cause the gains of amplifiers 44 to be reduced as the temperature of blood 15 rises during thawing. As a result, transmit/receive antennas 40 and radiometers 46 passively and non-invasively detect the emissivity of blood 15, and accurately control the level of transmitted power as blood 15 gradually thaws from a solid frozen body, to a semi-liquid slushy condition, and finally to its liquid condition. Among other advantages, this allows the power level applied by transmit/receive antennas 40 to blood 15 to be relatively high when the blood temperature is low (e.g., when blood 15 is frozen solid or is a "slush" of ice and fluid), and then gradually decreased as blood 15 changes to its liquid state and is warmed.

The gain of each amplifier 44 is variable between 0 dB and 20 dB in response to the control signal applied by the associated radiometer 46. This allows the level of microwave energy radiated by each transmit/receive antenna 40 to be adjusted between 375 milliwatts and approximately 38 watts. As mentioned above, the transmitted microwave energy has a frequency of 2.45 GHz. Radiometers 46 (available from Microwave Medical Systems, Littleton, Mass.) detect the radiant energy from blood 15 at a different frequency—such as 4.0 GHz. As discussed below, transmit/receive antennas 40 are configured to support energy propagation over this frequency range, while isolating signals applied to radiometers 46 from the transmitted energy.

In order to reduce the cost and complexity of system 10, the gain control signals generated by radiometers 46 of heating elements 36 of antenna array 34 are applied via lines 47 to variable gain amplifiers 44 of corresponding heating elements 36 of array 35. Thus, a single set of radiometers 46 controls the microwave energy level transmitted by both antenna arrays 34, 35 in response to the detected radiant energy.

The microwave energy produced by source 18 is applied equally to antenna arrays 34, 35 by 3 dB coupler 60. Moreover, each antenna array 34, 35 includes a microwave power distribution network 48 for equally dividing the applied microwave energy among the eight heating elements 36 of each array 34, 35. A 3 dB coupler 58 at the input of distribution network 48 divides the applied microwave energy equally between rows 41a, 41b of heating elements 36. And each row 41a, 41b includes three series-connected Wilkinson couplers 50, 52, 54 with coupling values of 6 dB, 4.8 dB, and 3.0 dB, respectively, for applying the microwave energy to inputs 56 of variable gain amplifiers 44 of heating elements 36. The microwave signal generated by source 18 has a power level of approximately 3 watts. Thus, it is seen that the coupling values discussed above result in approximately 380 milliwatts of microwave energy being provided to each variable gain amplifier 44.

A coaxial rotary joint 62 (FIG. 1), serving as one of the hinges between door panels 20, 22, is connected between coupler 60 and power distribution network 48 (not shown) of antenna array 35. Rotary joint 62 (available from Sage Laboratories, Natick, Mass.) allows door panels 20, 22 to pivot relative to each other without disrupting the electrical connections to array 35.

The maximum power level of 38 watts generated by each heating element 36 is based on the energy required to thaw a standard bag 14 holding 682 ml of glycerolized red blood cells 15 stored at a temperature of −65° C. The following relationship is used to determine the required energy (Q) under these circumstances:

$$Q = mc\Delta T \text{ calories}$$

where:

Q=energy required to thaw blood
m=mass (volume * specific gravity)
c=specific heat
$\Delta T$=65° C.

The specific gravity and specific heat of blood 15 are approximately those of water (i.e., 1 gm/cm$^3$ and 1 cal/gm° C., respectively). The use of the above relationship for approximating the required power and time for thawing assumes that any changes in the loss tangent and density as the blood changes from solid to liquid are immaterial. Substituting the above values of specific gravity and specific heat into the above formula, the energy (Q) required to thaw the blood is 44.3 kilocalories.

The electromagnetic power (P) needed to provide that amount of energy for a period of five minutes (the desired thawing period) is:

$$P \text{ (watts)} = \frac{(4.18 \text{ joules/cal.} * 44.3 \times 10^3 \text{ cal.})}{300 \text{ seconds}}$$

$$P = 620 \text{ watts.}$$

Dividing this power level equally among the sixteen individual waveguide heating elements 36 of arrays 34, 35 results in a power level of 38.75 watts for each heating element 36.

Figure 4:
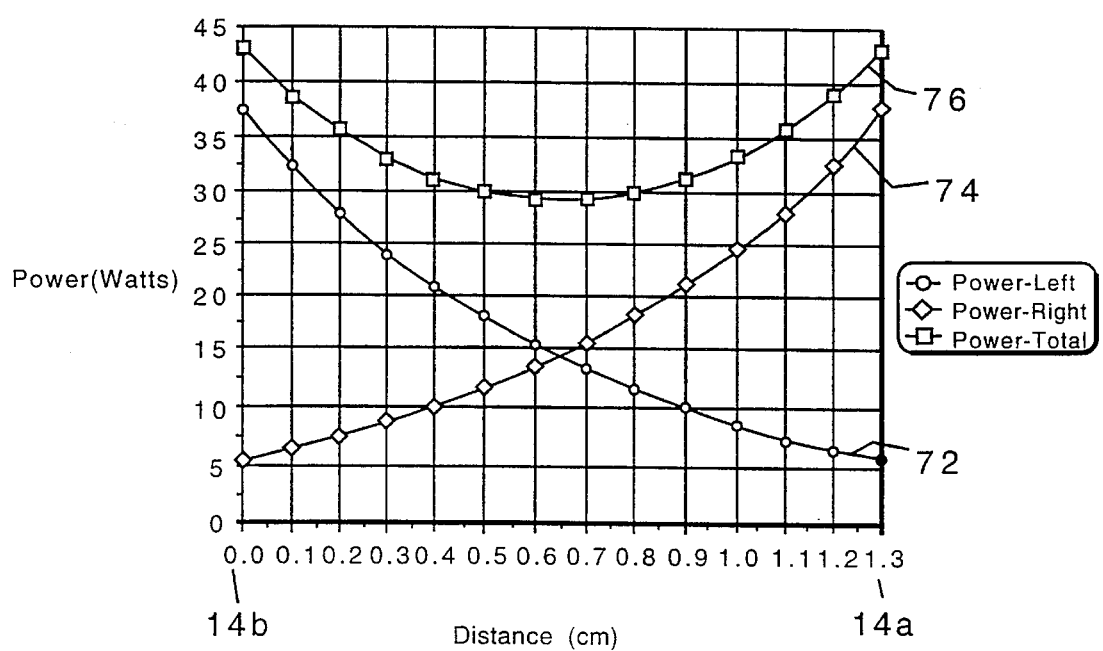
FIG. 4 illustrates the distribution of power (in watts) applied to opposite sides of a bag of fluid as a function of the depth (in cm.) of the bag.

Referring to FIG. 4, plot 70 shows the distribution of power from a pair of opposing antenna elements as a function of distance across the thickness of a bag 14 of 0.9% saline, a solution whose microwave characteristics closely approximate those of fresh frozen plasma (FPP). The measurement was performed using a test fixture which supported bag 14 between the pair of opposing antennas, each providing approximately 38 watts of power at 2.45 GHz. Curve 72 demonstrates that the level of power applied to the left broad surface 14b of bag 14 from the adjacent antenna decreases as the energy penetrates the saline, due to transmission loss through the saline. Curve 74 provides a similar profile for the opposing antenna. Curve 76 represents the sum of the power levels from each antenna at each depth position and shows that, with 38 watts transmitted from each antenna, approximately 30 watts of power is delivered to the centermost region of bag 14, while about 43 watts are applied near surfaces 14a, 14b of bag 14. The heating profile may be altered by offsetting the position of opposing antennas with respect to each other.

Figure 5:
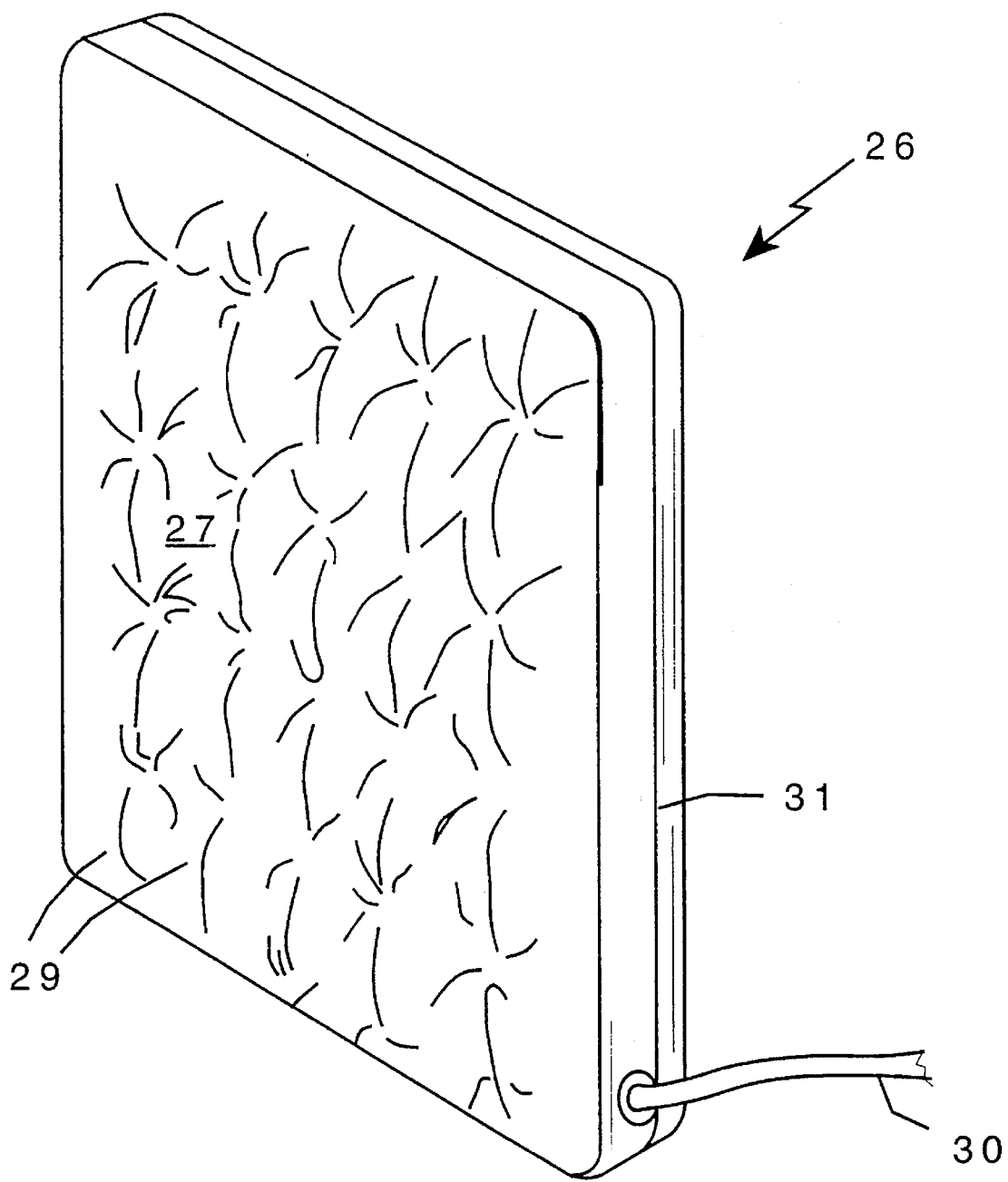
FIG. 5 is a perspective view of an inflation bladder used in the system of FIG. 1.

Referring to FIG. 5, one of bladders 26 is shown. Each bladder 26 is fabricated from a strong but expandable material, such as rubber. Bladder includes a matrix of rounded pads or cushions 29 formed on a front surface 27 for ensuring good contact between bladder 26 and bag 14, even when blood 15 is frozen within bag 14 in an irregular shape. A plate 31, made of a microwave transmissive material, is positioned on the rear surface of bladder 26 to provide rigidity and support to bladder 26 when inflated.

Bladder 26, when inflated, conforms to the shape of bag 14 and applies pressure to bag 14 for substantially maintaining the distribution of blood 15 within bag 14 during thawing. In other words, compression applied by bladder 26 helps prevent blood 15 (whether thawed or frozen) from settling into the bottom of bag 14 as the blood thaws. Instead, the applied pressure moves the thawed liquid blood portions from the central heated region of bag 14 toward peripheral regions of bag 14 while maintaining a uniform distribution of blood 15 within bag 14.

Bladder 26 is inflated with de-ionized water from compressor 32, which has low transmission loss, a high dielectric constant, and provides a well-matched impedance to the array elements at microwave frequencies. Moreover, de-ionized water is a coolant which draws heat away from blood near bag surfaces 14a, 14b, where the level of applied microwave energy is higher than in the interior of bag 14, as shown in FIG. 4. Providing cooling to surfaces 14a, 14b of bag 14 reduces the difference in temperature between those regions of blood 15 near surfaces 14a, 14b and in the interior of bag 14. Front surface 27 of bladder 26 may be fabricated or coated with a thermally conductive material for drawing heat away from surfaces 14a, 14b of bag 14 during thawing and into the coolant used to inflate bag 14.

Figure 6:
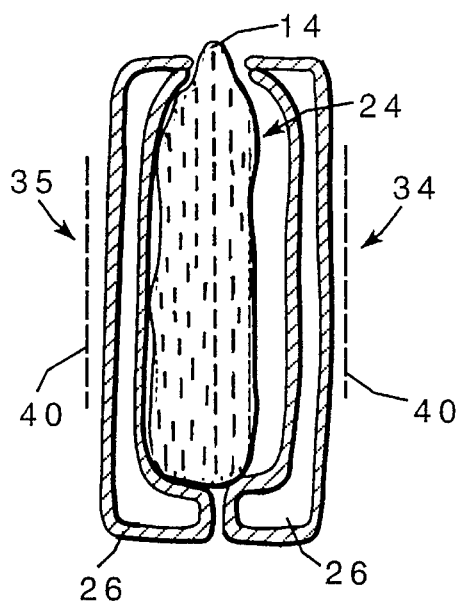
FIGS. 6–9 illustrate the thawing of a bag of blood product in cross-sectional side views.
Figure 7:
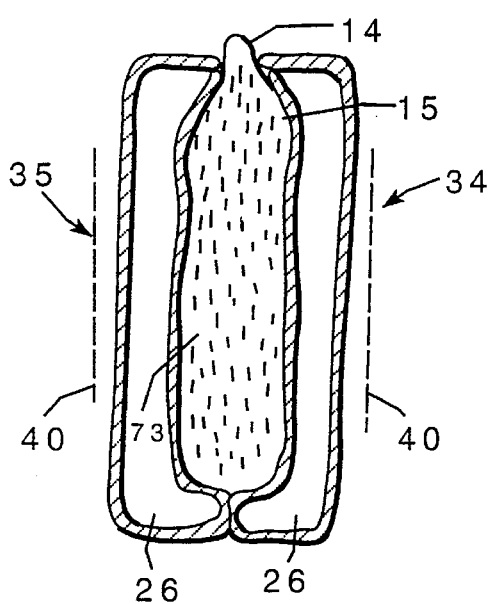
Figure 8:
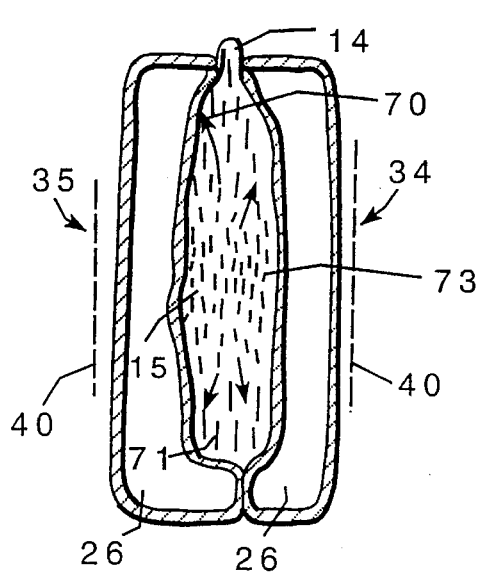

Referring to FIGS. 6–9, a bag 14 of frozen blood 15 is thawed using the system described above in conjunction with FIG. 1 as follows. As shown in FIG. 6, frozen bag 14 of blood (which typically has outer surfaces with a number of furrows and wrinkles) is positioned within one side of pressure infusion chamber 24. Then, doors 20, 22 are closed and locked so that arrays 34, 35 face the broad surfaces 14a, 14b of bag 14. Note that arrays 34, 35 are positioned adjacent the central region, rather than the periphery, of bag 14. As shown by FIG. 6, air spaces are typically present between bag 14 and bladders 26 due to the wrinkles on the surface of bag 14.

When triggered by a command from the user, computer 38 activates compressor 32 to begin inflating bladders 26. Bladders 26 are inflated to a preselected pressure level sufficient to cause both bladders 26 to fully contact broad surfaces 14a, 14b of bag 14 with no air spaces between bag 14 and bladders 26 bag 14 (FIG. 7) and to maintain the distribution of blood 15 within bag 14 during thawing. When the preselected pressure level is reached, computer 38 energizes microwave power source 18, thereby causing microwave energy to be applied to heating elements 36 of arrays 34, 35.

Initially, the emissivity of blood 15 is relatively low, due to its low temperature. Thus, the gains of amplifiers 44 are adjusted to their maximum levels by the control signals produced by radiometers 46. As a result, the maximum level of microwave power (e.g., 38 watts) is transmitted from each waveguide heating element 36 to heat that portion of frozen blood 15 located in the central region of bag 14. As blood 15 begins to thaw, it first turns to slush and then very gradually becomes liquid. It is only when blood 15 begins to change to its liquid state that its temperature—and thus its emissivity—begins to rise appreciably. The increase in emissivity is detected by radiometers 46, which respond by decreasing the gains of variable gain amplifier 44 thereby lowering the level of applied microwave energy to bag 14. Adjusting the gains of amplifiers 44 individually with control signals derived from the corresponding transmit/receive antenna 40 allows more (or less) microwave power to be applied to localized areas of blood 15, as needed.

The pressure applied by bladders 26 maintains a uniform distribution of blood 15 within bag 14 and causes thawed liquid portions 71 to be squeezed out of the central region of bag 14 to the periphery of bag 14 (in the direction of arrows 70 of FIG. 8), while retaining slush and frozen portions 73 of blood 15 in the central region. As a result, arrays 34, 35 can continue to direct thawing energy where it is needed—to slush/frozen portions 73—while sparing liquid portions 71 from excessive heating.

Figure 9:
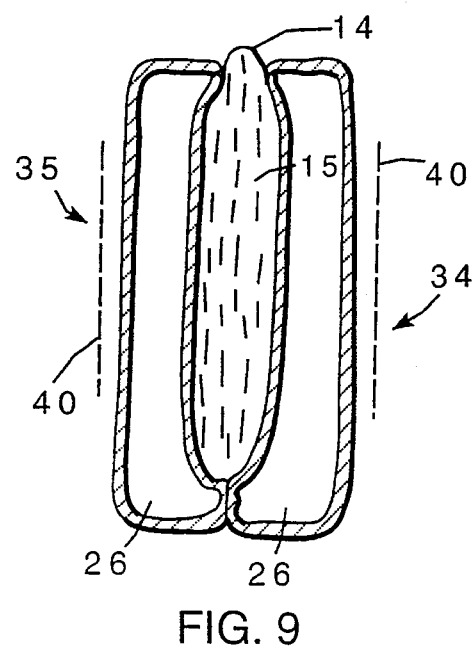

Inflated bladders 26 are in continuous contact with bag 14 and pressure is maintained so that bag 14 has a substantially uniform thickness throughout the thawing operation. Bag 14 is centrally and vertically positioned between antenna arrays 34, 35 to allow any air within bag 14 to rise to its top end. When the monitored temperature indicates that blood 15 has completely thawed, computer 38 deactivates source 18, and microwave power to antenna arrays 34, 35 is removed (FIG. 9). Upon opening doors 20, 22 bladders 26 are automatically deflated.

Figure 10:
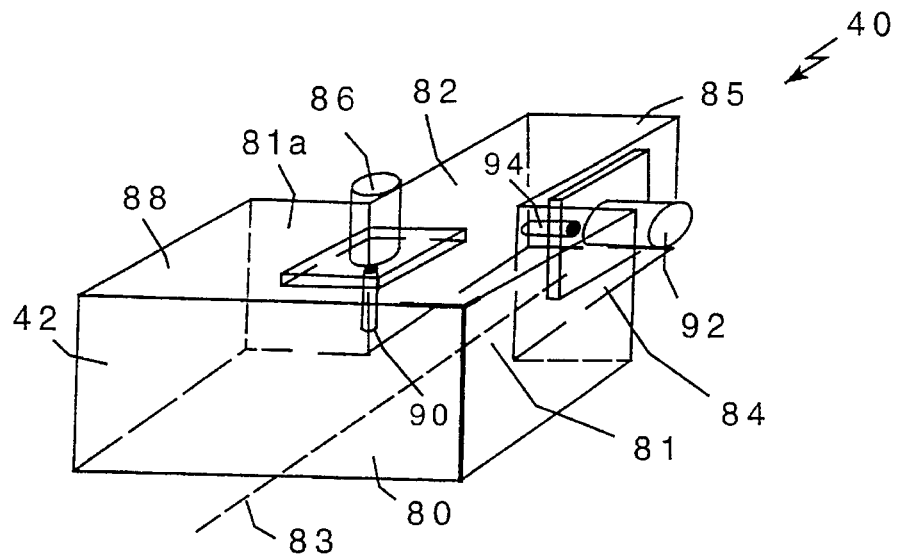
FIG. 10 is a perspective view of a transmit/receive antenna of the system of FIG. 1.
Figure 11:
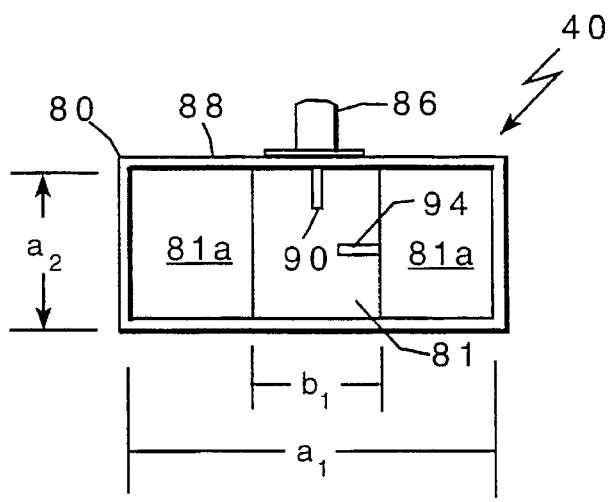
FIG. 11 is a front view of the transmit/receive antenna of FIG. 10.
Figure 12:
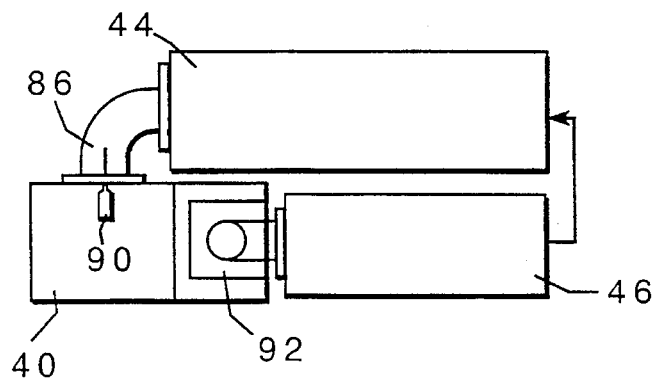
FIG. 12 is an end view of an antenna array element of the system of FIG. 1.

Referring to FIGS. 10–12, transmit/receive antenna 40 includes a rectangular receive waveguide 82 coupled to a rectangular transmit waveguide 80 through an opening 81 in one wall 81a of transmit waveguide 80. Transmit and receive waveguides 80, 82 share a common axis 83 and a common aperture 42 (the open face of waveguide 80). Transmit and receive waveguides 80, 82 have dimensions (width and height) selected so that the 4.0 GHz radiant energy received by radiometer 46 is isolated from the transmit microwave energy at 2.45 GHz.

For the $TE_{10}$ mode of transmission (the dominant mode of transmission in rectangular waveguide), a rectangular waveguide acts as a high pass filter with a cutoff frequency ($f_c$) determined by the following relationship:

$$f_c = \frac{c}{2d\sqrt{\epsilon_r}}$$

where c=velocity of light in free space;

d=the dimension of the waveguide transverse to the orientation of the electric field for the the signal of interest; and $\epsilon_r$=dielectric constant of the region within the waveguide. The $TE_{xy}$ (transverse electric) designation means that for this mode of propagation, the direction of the electric field is transverse to the direction of propagation (the subscripted numerals indicate the number of half sine wave variations of the electric field components in the x and y directions, respectively). Thus, for the $TE_{10}$ mode, only one half sine wave variation propagates in the x direction with none propagating in the y direction.

Referring to FIG. 11, a dimension ($a_1$) of transmit waveguide 80 is substituted in the above relationship to provide a cutoff frequency for transmit waveguide 80 below the frequency of the transmitted microwave energy (2.45 GHz). Thus, transmit waveguide 80 propagates the transmit microwave energy at 2.45 GHz to blood 15 and also supports the propagation of the radiant energy from blood 15 at 4.0 GHz. On the other hand, dimension ($a_2$) of receive waveguide 82 is selected to provide a cutoff frequency above the 2.45 GHz transmit energy, but below the 4.0 GHz radiant energy so that radiant energy at 4.0 GHz propagates, and the transmit energy at 2.45 GHz is attenuated, within receive waveguide 82.

Receive waveguide 82 is oriented orthogonally with respect to transmit waveguide 80. In other words, receive waveguide 82 is rotated 90° with respect to transmit waveguide 80 so that dimension ($a_1$) of transmit waveguide 80 is perpendicular to dimension ($a_2$) of receive waveguide 82. In this embodiment, dimension ($a_2$) of receive waveguide 82 is selected to be equivalent to the height of transmit waveguide 80. With this configuration, the orientation of the $TE_{10}$ mode electric field of the 2.45 GHz transmit energy propagating in transmit waveguide 80 is orthogonal to the orientation of the $TE_{10}$ mode electric field of the 4.0 GHz radiant energy propagating in receive waveguide 82. This orthogonal configuration of waveguides 80, 82 provides further isolation between the transmit energy at 2.45 GHz and the received radiant energy at 4.0 GHz. In addition, the larger aperture of transmit waveguide 80 serves as an antenna horn for the radiant energy at 4.0 GHz propagating to receive waveguide 82.

Dimension ($b_1$), which defines the width of opening 81, is also selected to provide a cutoff frequency above 4.9 GHz, the second harmonic of the transmit energy at 2.45 GHz, so that the second harmonic is substantially attenuated within receive waveguide 82. Dimension ($b_1$) also limits propagation of both the transmit energy (2.45 GHz) and radiant energy (4.0 GHz) oriented transverse to radiant energy propagating in receive waveguide in the $TE_{10}$ mode, (i.e., the $TE_{01}$ mode).

A transmit port 86, in the form of a coaxial connector, is mounted on a wall 88 of transmit waveguide 80, and includes a probe 90 extending vertically into waveguide 80 for applying the microwave transmitted energy within transmit waveguide 80 in the $TE_{10}$ mode. A receive port 92 (also in the form of a coaxial connector) is mounted to a side wall 84 of orthogonally coupled receive waveguide 82, and includes a probe 94 that extends horizontally into waveguide 82 to receive the radiant energy in the $TE_{10}$ mode. Probes 90, 94 are both positioned a distance of about one quarter wavelength, at the transmit and receive frequencies, from walls 81a, 85, respectively, so that the transmitted and radiant energy is maximally coupled between transmit and receive ports 86, 92 and respective waveguides 80, 82.

It is important to note that the amplitude of the transmitted microwave signal is generally several orders of magnitude higher than the received radiant energy, and a significant amount of attenuation is required to reduce the transmitted signal to a level below that of the radiant energy. Although much of the attenuation is provided by the frequency cutoff effect associated with the width of opening 81, the orthogonal arrangement of waveguides 80, 82 provides additional isolation between transmit port 86 and receive port 92 and, as a result, the sensitivity of radiometer 46 in receiving the radiant energy is increased.

The interior regions of both waveguides 80, 82 are filled with a dielectric material having a relatively high dielectric constant (e.g., $\epsilon_r$=2.55) for allowing the dimensions of waveguides 80, 82 to be decreased relative to the dimensions that would be needed if air were to be used as the dielectric. The result is a highly more compact (i.e., low profile) antenna 40. Dielectrically loading waveguide 80 also provides a smoother surface for contacting inflation bladders 26.

Other embodiments are within the scope of the claims.

Figure 13:
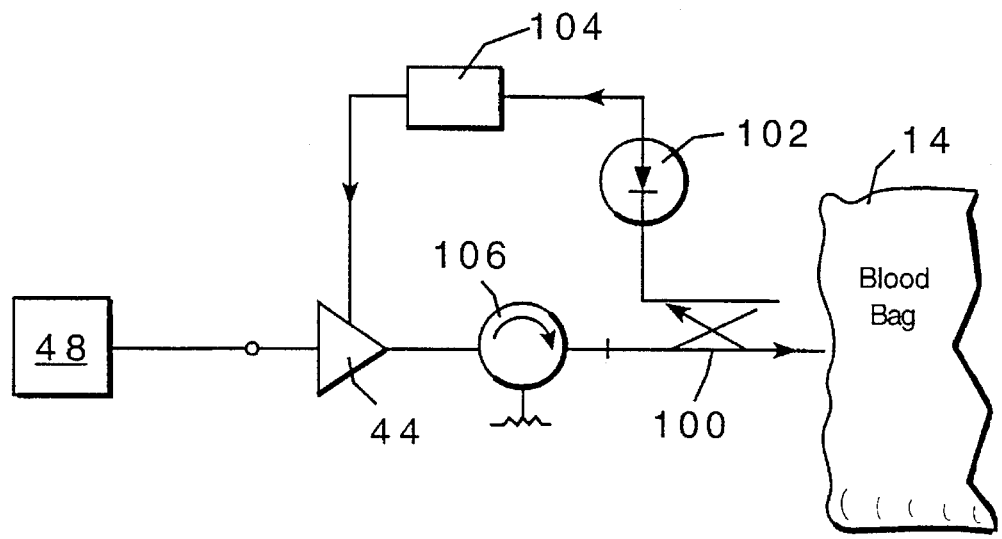
FIG. 13 is a schematic diagram of an alternative embodiment of the radiation circuit of the system of FIG. 1.

For example, as shown in FIG. 13, output power control of heating array elements 36 may be achieved through the measurement of reflection coefficient, rather than emissivity. With this approach, the dual mode frequency operation (i.e., transmitting at one frequency and receiving at a different frequency) as described above need not be used. Instead, the level of transmitted warming energy from variable gain amplifier 44 is based on the amount of the transmitted energy reflected from blood 15 during the thawing process.

In this embodiment, a waveguide directional coupler 100 is used to transmit the energy from amplifier 44 to bag 14 and to couple a relative portion of the reflected energy (at the same frequency as the transmitted energy) to a microwave detector 102. The ratio of the reflected power to the power incident on the bag, commonly referred to as the reflection coefficient, changes dramatically as the impedance of blood 15 changes during thawing. With this approach, the waveguide impedance of coupler 100 is initially matched to the intrinsic impedance of blood 15 in its frozen state. As blood 15 begins to thaw, the impedance becomes slightly mismatched, resulting in an increase in reflected energy; the impedance mismatch becomes significant as blood 15 approaches its liquid state, and thus the level of the reflected energy rises markedly.

The reflected energy is rectified by detector 102 and applied to a signal conditioning circuit 104 for generating a gain control signal for amplifier 44 which is inversely proportional to the reflected energy level. That is, the gain of amplifier 44 is decreased as the reflected energy level increases.

A three-port ferrite isolator 106 connected between amplifier 44 and the throughput arm of coupler 100 absorbs reflected energy that leaks through coupler 100. Isolator 106 also isolates amplifier 44 from the changing impedance of blood 15. One important consideration is that the change in reflection coefficient as blood thaws is offset, to some extent, by the fact that the density or specific gravity of the blood becomes smaller as it thaws, resulting in a correspondingly greater amount of energy per degree of temperature change as the blood thaws from a solid to a liquid.

Figure 14:
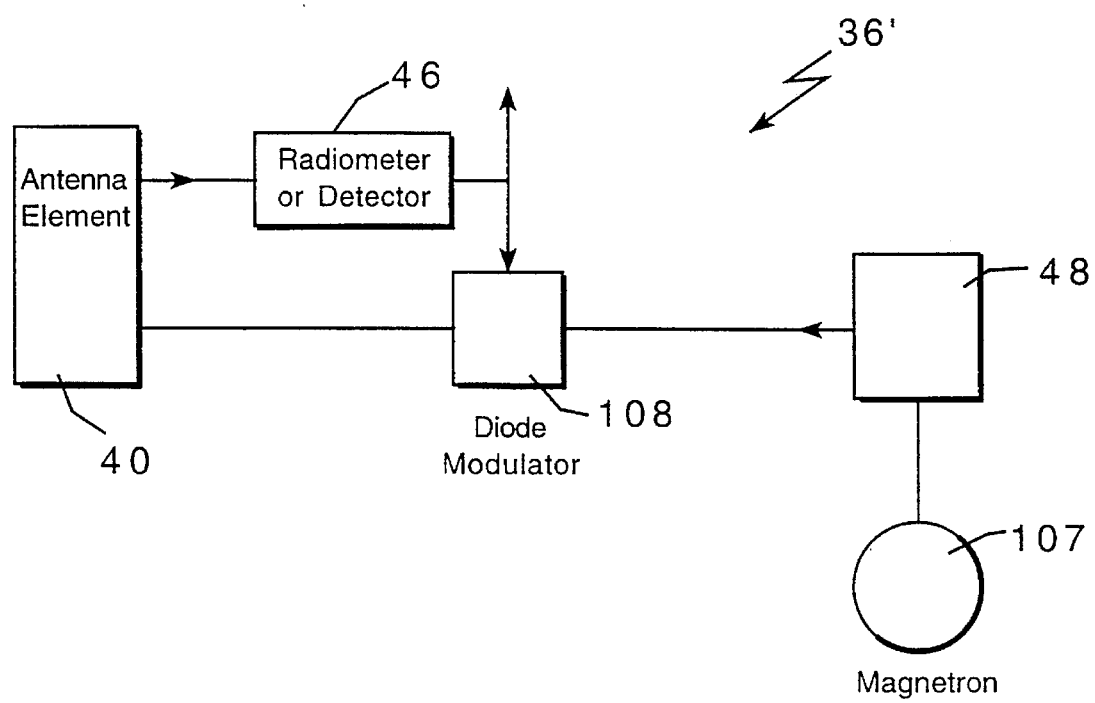
FIG. 14 is a schematic diagram of an alternative embodiment of the power control circuit of the system of FIG. 1.

Referring to FIG. 14, variable gain amplifier 44 may be replaced with a diode switch modulator 108, triggered by the control signal produced by radiometer 46 or detector 102. Modulator 108 (available from Microwave Medical Systems, Littleton, Mass.) applies the microwave energy from distribution network 48 to antenna element 40 as a series of pulses. Modulator 108 adjusts the duty cycle of the pulses (i.e., the ratio between the width of the pulses and the time between pulses) in response to the level of the control signal to modulate the transmitted power level.

During the period when modulator 108 is "off" the input power provided by a high power magnetron 107 is reflected back into distribution network 48 where it is absorbed by the terminated ports of couplers 50, 52, 54 (FIG. 3). To ensure that each heating element 36' coupled to distribution network 48 is capable of delivering the necessary 38 watts at 2.45 GHz, high power magnetron 107 is required to provide approximately 600 watts of continuous wave power. A magnetron and power supply used in a conventional microwave oven can be modified for use with this approach.

In still other embodiments, a vibration mechanism may also be coupled to pressure infusion chamber 24 to agitate and encourage mixing of the blood during thawing. It is generally desirable to maintain the displacement and frequency of the vibration mechanism (e.g., less than ⅛" displacement at 400 Hz) below noticeable noise levels.

Other configurations are also within the scope of the claims. For example, the number of heating elements and the array pattern (e.g., the positions of and the spacing between the array elements) may be varied to provide a desired heating profile. The size and geometry of transmit and receive waveguides 80, 82 may also be changed to operate at different frequencies within, for example, the microwave range of 300 MHz to 3.0 GHz, or in different waveguide modes. The waveguide components including transmit/receive antenna 40 and the couplers of distribution network 48 can also be replaced with ridge waveguide, integrated finline structures or planar printed circuits (e.g., suspended substrate circuits) which will reduce the size and, in some cases, the cost of the thawing apparatus.

Inflatable bladders 26 may be inflated with a gas, liquid, or powder to compress bag 14 within pressure infusion chamber 24. It is desirable that the medium used to inflate bladders 26 have a low transmission loss at both the transmit and receive frequencies of operation so that energy applied from or radiated to the antenna arrays 34, 35 is not absorbed. Moreover, the dielectric constant of the medium should be approximately that of blood 15 so that its intrinsic impedance is closely matched to the impedance of the heating elements 36.

Figure 15:
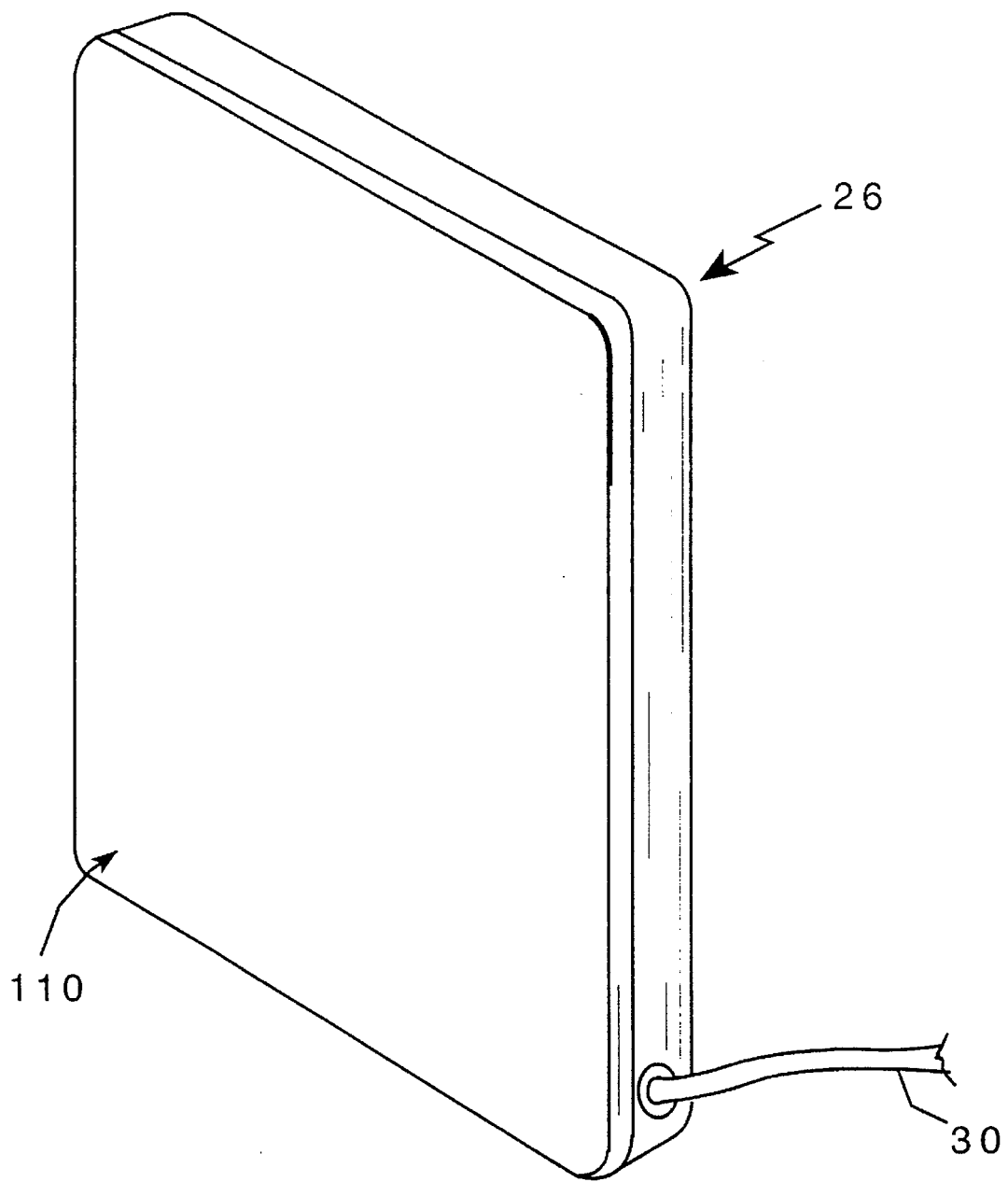
FIG. 15 is an alternative embodiment of the inflation bladder.

Referring to FIG. 15, inflatable bladders 26 may also include a compression plate 110 positioned over front surface 27 and fabricated from a thermally conductive material (e.g., BeO ceramic). Compression plate 110 provides better cooling of surfaces 14a, 14b of bag 14 and, thus, a more uniform temperature distribution of blood 15 between surfaces 14a, 14b.

In certain applications, the heating elements may time-share a common radiometer 46. On the other hand, to provide greater individual control, heating elements 36 of array 35 may include their own radiometers 46. A bandpass filter may be used with radiometer 46 to attenuate outside of the band of the radiometer, which includes signals at the transmitted frequency.

The system for thawing the red blood cells is equally applicable for thawing other types of blood products, including fresh frozen plasma and frozen platelets. Plasma and platelets, unlike red blood cells, do not require the addition of glycerol, and therefore can be stored at higher temperatures (−18° C.). For these types of blood products, a smaller, lower power, thawing unit may be used, perhaps having only a single heating array positioned to provide heating from only one side of the bag of blood product.

What is claimed is:

1. Apparatus for thawing blood product stored within a container, said apparatus comprising:

a housing having a cavity configured to receive said container of said blood product;

a microwave energy source which produces warming energy at a selected frequency to thaw the blood product within the container;

a plurality of antennas coupled to said microwave energy source, said antennas being disposed within said housing adjacent to said cavity and positioned to transmit said energy from said microwave energy source into the cavity and to respectively different regions of said blood product within the container, one of said antennas being configured to receive electromagnetic energy corresponding to an emissivity of said blood product at a frequency different than said selected frequency; and a control circuit for changing levels of said warming energy transmitted by different ones of said plurality of antennas by selectively different amounts in response to said electromagnetic energy received by said one of said antennas.

2. The apparatus of claim 1 wherein a level of said electromagnetic energy from said blood product indicates a degree to which said blood product is thawed, said control circuit reducing said level of warming energy transmitted to the blood product as the thawing of said blood product increases.

3. The apparatus of claim 2 wherein said control circuit includes a radiometer responsive to said emissivity for changing said level of said warming energy transmitted to said blood product.

4. The apparatus of claim 3 wherein said frequency of said warming energy is between 300 MHz and 3.0 GHz.

5. The apparatus of claim 2 wherein said source includes a variable gain amplifier, said circuit controlling the gain of said amplifier in response to said level of said electromagnetic energy.

6. The apparatus of claim 2 wherein said source further includes a modulator for transmitting said warming energy to said blood product in a series of pulses, said control circuit including circuitry responsive to said electromagnetic energy for changing a duty cycle of said pulses thereby to change the level of said warming energy transmitted to said blood product.

7. The apparatus of claim 1 wherein said control circuit comprises circuitry, responsive to said received electromagnetic energy, for individually changing the level of energy transmitted from each of said antennas.

8. The apparatus of claim 1 wherein each one of said plurality of antennas receives said electromagnetic energy, said control circuit comprising circuitry responsive to the electromagnetic energy received by each said antenna for individually changing the level of energy transmitted by said plurality of antennas.

9. The apparatus of claim 1 wherein said plurality of antennas are proximately positioned and spaced from each other along outer surfaces of the container in which the blood product is disposed.

10. A method of thawing blood product stored within a container, said method comprising the steps of:

a) positioning said container of blood product within a cavity of a housing supporting a plurality of antennas;

b) directing microwave warming energy at a selected frequency from said plurality of antennas into the cavity and to different regions of said blood product within the container, each antenna associated with one of said regions;

c) sensing electromagnetic energy corresponding to an emissivity said blood product at a frequency different than said selected frequency, a level of said electromagnetic energy indicating the degree to which said blood product is thawed; and d) changing levels of said warming energy directed by different ones of said antennas by selectively different amounts in response to the sensed level of said electromagnetic energy.

11. The method of claim 10 wherein said warming energy has a frequency between 300 MHz and 3.0 GHz.

12. The method recited in claim 10 wherein said step of changing levels of said warming energy includes modulating the warming energy as a series of pulses and changing the duty cycle of said pulses to change the level of said warming energy transmitted to said blood product.

13. The method recited in claim 10 wherein said step of changing levels of said warming energy includes individually changing the level of warming energy directed to the blood product from said plurality of antennas in response to said electromagnetic energy received by one of said antennas.

14. The method recited in claim 10 further comprising positioning said plurality of antennas in spaced relation along outer surfaces of the container in which the blood product is disposed.

* * * * *